United States Patent

Kagano et al.

[11] Patent Number: 5,856,504
[45] Date of Patent: Jan. 5, 1999

[54] PROCESSES FOR PRODUCING ISOTHIAZOLE DERIVATIVES

[75] Inventors: Hirokazu Kagano; Hiroshi Goda; Mikio Yamamoto; Shigeki Sakaue; Miki Toudou, all of Hyogo, Japan

[73] Assignee: Sumitomo Seika Chemicals Co., Ltd., Hyogo, Japan

[21] Appl. No.: 836,697

[22] PCT Filed: Dec. 4, 1995

[86] PCT No.: PCT/JP95/02484

§ 371 Date: May 19, 1997

§ 102(e) Date: May 19, 1997

[87] PCT Pub. No.: WO96/17834

PCT Pub. Date: Jun. 13, 1996

[30] Foreign Application Priority Data

Dec. 8, 1994 [JP] Japan .................................. 6-331731

[51] Int. Cl.$^6$ ................................................. C07D 275/04
[52] U.S. Cl. .............................................. 548/207; 544/368
[58] Field of Search ............................ 548/207; 544/368

[56] References Cited

U.S. PATENT DOCUMENTS 4,590,196  5/1986  Smith et al. ............................ 514/253

FOREIGN PATENT DOCUMENTS 3530089  3/1986  Germany .
63-83067  4/1988  Japan .
63-83085  4/1988  Japan .

OTHER PUBLICATIONS

Becke et al., Liebigs Annalen Der Chemie, 729: 146–151 (1969).
Ricci et al., Ann. Chim. (Rome), 53(5), 577–587 (1963).
Meth–Cohn et al., Synthesis (1), 58–60 (1978).
McKinnon et al., Can. J. Chem. 66, 1405–9 (1988).
Rahman et al., J. Chem. Soc. Perkin Trans. I, 385–90 (1984).

*Primary Examiner*—Deborah C. Lambkin
*Assistant Examiner*—Laura R. C. Lutz
*Attorney, Agent, or Firm*—Birch, Stewart Kolasch & Birch, LLP

[57] ABSTRACT

A method for producing a 1,2-benzisothiazole characterized by treating a 2-(alkylthio)benzaldehyde oxime with a halogen compound; a method for producing a 3-halo-1,2-benzisothiazole characterized by treating a 1,2-benzisothiazole with a halogenating agent; and a method for producing a 1-(1,2-benzisothiazol-3-yl)piperazine characterized by reacting the obtained 3-halo-1,2-benzisothiazoles with a piperazine. By the method of the present invention, 1,2-benzisothiazoles and 3-halo-1,2-benzisothiazoles, which are useful as intermediates for pharmaceutical compositions such as psychotropic agents, and 1-(1,2-benzisothiazole-3-yl)piperazines synthesized therefrom can be obtained in a high yield without using expensive starting materials by shorter and simpler process than conventional methods.

15 Claims, No Drawings

PROCESSES FOR PRODUCING ISOTHIAZOLE DERIVATIVES

This application is a 371 of PCT/JP95/02484 filed Dec. 4, 1995.

TECHNICAL FIELD

The present invention relates to a novel method for producing 1,2-benzisothiazoles and 3-halo-1,2-benzisothiazoles using 2-(alkylthio)benzaldehyde oximes as starting materials. The present invention further relates to a novel method for producing 1-(1,2-benzisothiazol-3-yl)piperazines using 3-halo-1,2-benzisothiazoles as starting materials. 1-(1,2-benzisothiazol-3-yl)piperazines are useful compounds as therapeutic agents for the central nervous system disorders (antipsychotic agents) and neural relaxants, or intermediates for the production of these agents.

BACKGROUND ART

Conventionally, the known methods for producing 1,2-benzisothiazoles and 3-halo-1,2-benzisothiazoles include the following:

(A) Ann. Chim. (Rome) 53(5), 577–87(1963)

(A) Ann. Chim. (Rome) 53(5), 577–87 (1963)

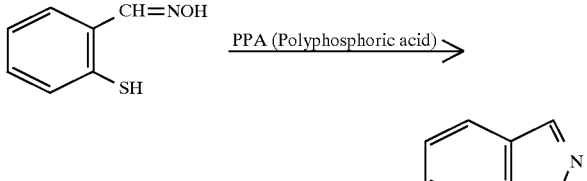

(Yield Not Disclosed)

(B) Synthesis (1), 58–60 (1978)

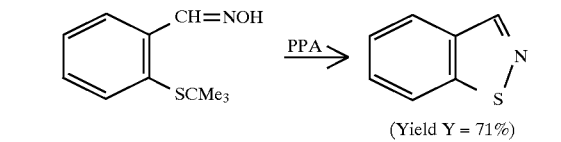

(Yield Y = 71%)

(C) Ger. Offen. 3530089, (1986)

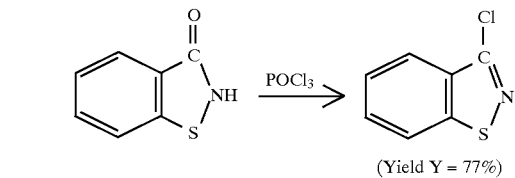

(Yield Y = 77%)

(D) Japanese Patent Laid-Open No. 63-83085

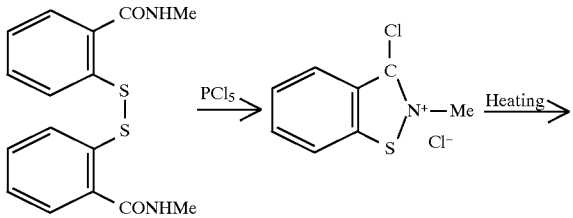

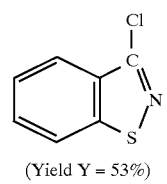

(Yield Y = 53%)

However, the above known methods have the following drawbacks:

In (A) and (B), examples of methods for producing 1,2-benzisothiazoles are disclosed. Since there are no disclosures concerning a method by which 2-substituted benzaldehyde oximes, the starting materials, can be obtained on an industrial scale, details are unknown. Also, the yields by these methods are not high.

In (C) and (D), examples of methods for producing 3-chloro-1,2-benzisothiazoles are disclosed. The method of (C) uses expensive 1,2-benzisothiazol-3-ones as the starting materials, and gives a poor yield. The method of (D) cannot be said to be industrially advantageous because this method requires the use of expensive thiosalicylic acid as the starting material and achieves an unsatisfactory yield.

As mentioned above, with any known methods, it has been difficult to advantageously produce 1,2-benzisothiazoles and 3-halo-1,2-benzisothiazoles on an industrial scale.

DISCLOSURE OF THE INVENTION

In view of the above situation, the present inventors have made intensive studies to provide a simple and economically advantageous method for producing 1,2-benzisothiazoles and 3-halo-1,2-benzisothiazoles on an industrial scale without using expensive materials. As a result, the inventors have found that a 1,2-benzisothiazole represented by the general formula (II) can be obtained by treating a 2-(alkylthio) benzaldehyde oxime represented by the general formula (I) with a halogen compound.

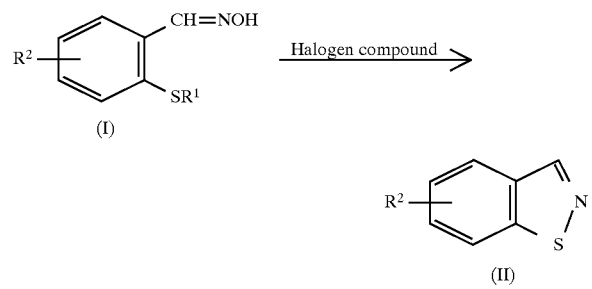

wherein $R^1$ represents an alkyl group having 1 to 4 carbon atoms; and $R^2$ represents a hydrogen atom, an alkyl group having 1 to 4 carbon atoms, an alkoxy group having 1 to 4 carbon atoms, a nitro group, a carboxyl group or an ester thereof, or a halogen atom.

The present inventors have further found that a 3-halo-1,2-benzisothiazole represented by the general formula (III) can be obtained by the reaction between a 1,2-benzisothiazole represented by the general formula (II) and a halogenating agent.

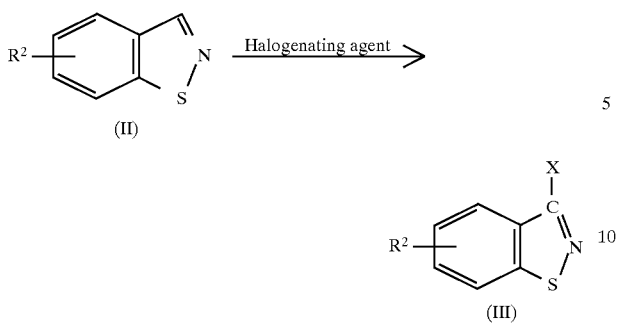

wherein X represents a chlorine atom or a bromine atom; and $R^2$ represents a hydrogen atom, an alkyl group having 1 to 4 carbon atoms, an alkoxy group having 1 to 4 carbon atoms, a nitro group, a carboxyl group or an ester thereof, or a halogen atom.

Also, the present inventors have found that even when the above two reactions are successively carried out, the remainder of a halogen compound which is used for the cyclization of the 2-(alkylthio)benzaldehyde oxime does not affect the subsequent halogenation process and, therefore, the above two reactions can be carried out in a one-pot process. Specifically, the present inventors have found that a 3-halo-1,2-benzisothiazole represented by the general formula (III) can be obtained from a 2-(alkylthio)benzaldehyde oxime represented by general formula (I) in a one-pot process. The present inventors have completed the present invention after they have further found that a 1-(1,2-benzisothiazol-3-yl) piperazine represented by the general formula (V) can be obtained by the reaction between a 3-halo-1,2-benzisothiazole represented by the general formula (III) obtained by the production method of the present invention, and a piperazine represented by the general formula (IV).

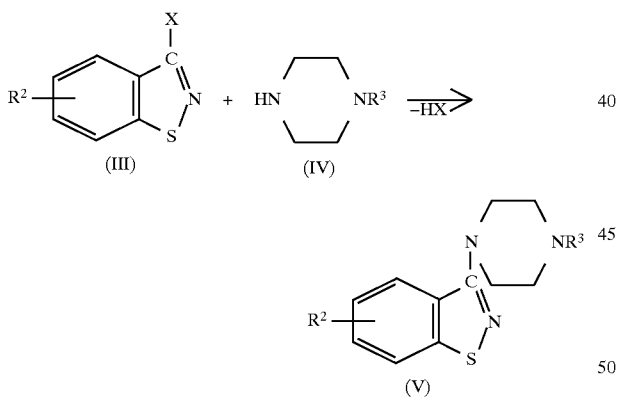

wherein X represents a chlorine atom or a bromine atom; $R^2$ represents a hydrogen atom, an alkyl group having 1 to 4 carbon atoms, an alkoxy group having 1 to 4 carbon atoms, a nitro group, a carboxyl group or an ester thereof, or a halogen atom; $R^3$ represents a hydrogen atom, an alkyl group having 1 to 6 carbon atoms, or a substituted alkylene group having 1 to 6 carbon atoms.

In brief, the gist of the present invention is concerned with:

(1) A method for producing a 1,2-benzisothiazole represented by the general formula (II), characterized by treating a 2-(alkylthio)benzaldehyde oxime represented by the general formula (I) with a halogen compound;

(2) The method described in (1) above, wherein the halogen compound is thionyl chloride;

(3) The method described in (1) above, wherein the halogen compound is phosphorus oxychloride;

(4) The method described in any one of (1) to (3) above, wherein the compound represented by the general formula (I) is 2-(methylthio)benzaldehyde oxime;

(5) A method for producing a 3-halo-1,2-benzisothiazole represented by the general formula (III), characterized by reacting a 1,2-benzisothiazole represented by the general formula (II) with a halogenating agent;

(6) The method described in (5) above, wherein the halogenating agent is chlorine or bromine;

(7) The method described in (5) above, wherein the halogenating agent is sulfuryl chloride;

(8) The method described in any one of (5) to (7) above, wherein the compound represented by the general formula (II) is 1,2-benzisothiazole;

(9) A method for producing a 3-halo-1,2-benzisothiazole represented by the general formula (III), characterized by
treating a 2-(alkylthio)benzaldehyde oxime represented by the general formula (I) with a halogen compound to give a 1,2-benzisothiazole represented by the general formula (II); and
reacting the 1,2-benzisothiazoles with a halogenating agent;

(10) The method described in (9) above, wherein the halogen compound is thionyl chloride;

(11) The method described in (9) above, wherein the halogen compound is phosphorus oxychloride;

(12) The method described in (9) above, wherein the halogenating agent is chlorine or bromine;

(13) The method described in (9) above, wherein the halogenating agent is sulfuryl chloride;

(14) The method described in any one of (9) to (13), wherein the compound represented by the general formula (I) is 2-(methylthio)benzaldehyde oxime; and

(15) A method for producing a 1-(1,2-benzisothiazol-3-yl)piperazine represented by the general formula (V), characterized by
treating a 2-(alkylthio)benzaldehyde oxime represented by the general formula (I) with a halogen compound to give a 1,2-benzisothiazole represented by the general formula (II);
reacting the obtained 1,2-benzisothiazoles with a halogenating agent to give a 3-halo-1,2-benzisothiazole represented by the general formula (III); and
reacting the 3-halo-1,2-benzisothiazoles with a piperazine represented by the general formula (IV).

BEST MODE FOR CARRYING OUT THE INVENTION

The present invention will be detailed below.

In the method of the present invention for producing a 3-halo-1,2-benzisothiazole, a 2-(alkylthio)benzaldehyde oxime used as a starting material can readily be obtained by the reaction of a corresponding 2-(alkylthio)benzaldehyde with a hydroxylamine. Thus, the present invention is characterized in that a 1,2-benzisothiazole can be produced by treating a 2-(alkylthio)benzaldehyde oxime which is readily obtained on an industrial scale with a halogen compound used as a cyclizing agent to facilitate a selective cyclization; that a 3-halo-1,2-benzisothiazole can be obtained in high yield by reacting a 1,2-benzisothiazole with a halogenating agent without using expensive starting materials; and that a 3-halo-1,2-benzisothiazole can readily be obtained from a 2-(alkylthio)benzaldehyde oxime in a markedly high yield by successively carrying out the above two reactions in a one-pot process.

The present invention is further characterized in that a 1-(1,2-benzisothiazol-3-yl)piperazine can be produced by reacting the 3-halo-1,2-benzisothiazoles obtained by the present invention with a piperazine.

$R^1$ in the above general formula (I) represents an alkyl group having 1 to 4 carbon atoms. Alkyl groups represented by $R^1$ are exemplified by methyl, ethyl, n-propyl, isopropyl, n-butyl, isobutyl, sec-butyl and tert-butyl groups.

Among the above, a preference is given to methyl, ethyl, n-propyl, and tert-butyl groups for $R^1$.

$R^2$ in the general formulas (I), (II), (III) and (V) specifically represents a hydrogen atom, an alkyl group having 1 to 4 carbon atoms, an alkoxy group having 1 to 4 carbon atoms, a nitro group, a carboxyl group or an ester thereof, or a halogen atom.

Alkyl groups represented by $R^2$ are exemplified by methyl, ethyl, n-propyl, isopropyl, n-butyl, isobutyl, sec-butyl, and tert-butyl groups. Alkoxy groups represented by $R^2$ are exemplified by methoxy, ethoxy, propoxy, and butoxy groups. Esters of carboxyl group represented by $R^2$ are exemplified by methoxycarbonyl, ethoxycarbonyl, propoxycarbonyl, and butoxycarbonyl groups. Halogen atoms represented by $R^2$ are exemplified by a chlorine atom and a bromine atom.

Among the above, preferred examples of $R^2$ include a hydrogen atom, a chlorine atom, and a nitro group.

Specific examples of 2-(alkylthio)benzaldehyde oximes represented by the general formula (I) include:
2-(methylthio)benzaldehyde oxime,
2-(ethylthio)benzaldehyde oxime,
2-(n-propylthio)benzaldehyde oxime,
2-(tert-butylthio)benzaldehyde oxime,
5-methyl-2-(methylthio)benzaldehyde oxime,
5-butyl-2-(methylthio)benzaldehyde oxime,
4-methoxy-2-(methylthio)benzaldehyde oxime,
2-methylthio-3-nitrobenzaldehyde oxime,
4-chloro-2-(methylthio)benzaldehyde oxime,
4-carboxy-2-(methylthio)benzaldehyde oxime, and
4-methoxycarbonyl-2-(methylthio)benzaldehyde oxime.

Among the above examples, 2-(methylthio)benzaldehyde oxime, 2-(ethylthio)benzaldehyde oxime, 2-(n-propylthio) benzaldehyde oxime, and 2-(tert-butylthio)benzaldehyde oxime are preferably used because they are readily available.

Examples of the halogen compounds used in the process of obtaining a 1,2-benzisothiazole from a 2-(alkylthio) benzaldehyde oxime in the present invention include thionyl chloride, phosphorus oxychloride, phosphorus pentachloride, phosphorus trichloride, sulfuryl chloride, and sulfuryl bromide. In view of reaction selectivity, thionyl chloride and phosphorus oxychloride are preferably used. The halogen compound is used usually in an amount of 0.8 to 3.0 moles, preferably 1.0 to 2.0 moles, per mole of the 2-(alkylthio)benzaldehyde oxime. When the amount of the halogen compound is less than 0.8 times the mole, the amount of unchanged 2-(alkylthio)benzaldehyde oxime increases. On the other hand, even when the amount of the halogen compound exceeds 3.0 times the mole, any effects cannot be obtained corresponding to the amount added, making it economically disadvantageous.

The reaction solvents used in the process of obtaining a 1,2-benzisothiazole by the treatment with a halogen compound are not particularly limited as long as they are inert to the reaction. Examples include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene. Among them, monochlorobenzene and toluene are preferably used. The amount of the solvent used is usually 1 to 30 times the weight of the 2-(alkylthio)benzaldehyde oxime.

The reaction temperature is usually in the range of from −30° to 50° C., preferably −20° to 10° C. Reaction temperatures higher than 50° C. cause problems of side reactions. On the other hand, reaction rate undesirably lowers to an impractical level when the reaction temperature is less than −30° C. The reaction time is usually in the range between 1 and 40 hours, but it may vary depending on the reaction temperature and the kinds of reaction solvent.

The objective reaction product, 1,2-benzisothiazoles, can be isolated and purified from the reaction mixture as obtained above by a conventional method, i.e., by direct crystallization or by extraction and subsequent recrystallization, but the methods are not limited thereto.

In the present invention, the reaction mixture may be subjected to the subsequent process without isolating the 1,2-benzisothiazole obtained so as to produce the compound represented by the general formula (III) in a one-pot process.

Specific examples of 1,2-benzisothiazoles represented by the general formula (II), the objective compound, obtained by the above method are exemplified as follows:
1,2-benzisothiazole,
5-methyl-1,2-benzisothiazole,
5-butyl-1,2-benzisothiazole,
6-methoxy-1,2-benzisothiazole,
7-nitro-1,2-benzisothiazole,
6-chloro-1,2-benzisothiazole,
6-carboxy-1,2-benzisothiazole, and
6-methoxycarbonyl-1,2-benzisothiazole.

Examples of the halogenating agents used in the process of obtaining a 3-halo-1,2-benzisothiazole from a 1,2-benzisothiazole in the present invention include chlorine, bromine, sulfuryl chloride, sulfuryl bromide, phosphorus oxychloride, phosphorus pentachloride, and phosphorus trichloride. The halogenating agent is used usually in an amount of 0.8 to 3.0 moles, preferably 1.0 to 2.0 moles, per mole of the 1,2-benzisothiazole. When the amount of the halogenating agent is less than 0.8 times the mole, the amount of unchanged 1,2-benzisothiazole increases. On the other hand, even when the amount of the halogenating agent exceeds 3.0 times the mole, any effects corresponding to the amount added cannot be obtained, making it economically disadvantageous.

The reaction solvents used in the process of obtaining a 3-halo-1,2-benzisothiazole by the reaction with a halogenating agent are not particularly limited as long as they are inert to the reaction. Examples include hydrocarbons, such as n-hexane, n-heptane, cyclohexane, methylcyclohexane, benzene, toluene and xylene; and halogenated hydrocarbons, such as methylene chloride, 1,2-dichloroethane and chlorobenzene. The amount of the solvent is usually 1 to 30 times the weight of the 1,2-benzisothiazole. Also, the reaction solvent used in the process of obtaining a 1,2-benzisothiazole can successively be used as is in this process.

The reaction temperature is usually in the range of from 30° to 150° C., preferably 50° to 100° C. Reaction temperatures higher than 150° C. cause problems of side reactions. On the other hand, reaction rate undesirably lowers to an impractical level when the reaction temperature is less than 30° C. The reaction time is usually in the range between 1 and 30 hours, but it may vary depending on the reaction temperature and the kinds of reaction solvent.

The objective reaction product, 3-halo-1,2-benzisothiazoles, can be isolated and purified from the reaction mixture as obtained above by a conventional method, i.e., direct crystallization, distilling off of the solvent and then distillation under reduced pressure, or extraction and subsequent recrystallization, but the methods for isolation and purification are not limited thereto.

In the present invention, the reaction mixture may be subjected to the subsequent process without isolating the 3-halo-1,2-benzisothiazole obtained so as to produce the compound represented by the general formula (V) in a one-pot process.

Specific examples of the thus obtained reaction products, 3-halo-1,2-benzisothiazoles represented by the general formula (III), are exemplified as follows:
3-chloro-1,2-benzisothiazole,
3-bromo-1,2-benzisothiazole,
3-chloro-5-methyl-1,2-benzisothiazole,
5-butyl-3-chloro-1,2-benzisothiazole,
3-chloro-6-methoxy-1,2-benzisothiazole,
3-chloro-7-nitro-1,2-benzisothiazole,
3,6-dichloro-1,2-benzisothiazole,
6-carboxy-3-chloro-1,2-benzisothiazole, and
3-chloro-6-methoxycarbonyl-1,2-benzisothiazole.

The method for producing a 1-(1,2-benzisothiazol-3-yl)piperazine represented by the general formula (V) by the reaction of a 3-halo-1,2-benzisothiazole with a piperazine represented by the general formula (IV) is publicly known. However, the method of the present invention is industrially advantageous as compared with conventional methods by making it possible to obtain the objective product from an easily available starting material in a one-pot process which comprises a series of reactions comprising treating a 2-(alkylthio)benzaldehyde oxime represented by the general formula (I) with a halogen compound to give a 1,2-benzisothiazole represented by the general formula (II); treating the obtained product with a halogenating agent to give a compound represented by the general formula (III); and then treating the obtained product with a piperazine represented by the general formula (IV) to give a 1-(1,2-benzisothiazol-3-yl)piperazine represented by the general formula (V).

$R^3$ in the general formulas (IV) and (V) represents a hydrogen atom, an alkyl group having 1 to 6 carbon atoms, or a substituted alkylene group having 1 to 6 carbon atoms. Alkyl groups represented by $R^3$ are exemplified by methyl, ethyl, n-propyl, isopropyl, n-butyl, isobutyl, sec-butyl, tert-butyl, amyl, hexyl, and cyclohexyl groups. Substituted alkylene groups having 1 to 6 carbon atoms represented by $R^3$ are exemplified by imidobutylene, amidobutylene, and (5-indol)ethylene groups.

Specific examples of 1-(1,2-benzisothiazol-3-yl)piperazines represented by the general formula (V) include:
1-(1,2-benzisothiazol-3-yl)piperazine,
1-(5-methyl-1,2-benzisothiazol-3-yl)piperazine,
1-(6-methoxy-1,2-benzisothiazol-3-yl)piperazine,
3-(4-ethyl-1-piperazinyl)-1,2-benzisothiazole,
3-(4-n-butyl-1-piperazinyl)-1,2-benzisothiazole,
3-(4-cyclohexyl-1-piperazinyl)-1,2-benzisothiazole,
N-[4-{4-(1,2-benzisothiazol-3-yl)-1-piperazinyl}butyl] cyclohexane-1,2-dicarboxyimide, and
5-[2-{4-(1,2-benzisothiazol-3-yl)-1-piperazinyl}ethyl]-6-chloro-1,3-dihydro-2H-indol-2-one.

The present invention will be described in further detail by means of the following working examples, but the present invention is by no means restricted to these working examples.

EXAMPLE 1

Synthesis of 1,2-Benzisothiazole

In a 300 ml four-necked flask equipped with a stirrer, a thermometer, and a condenser, 100 g of monochlorobenzene was placed in advance, to which 33.4 g (0.2 mol) of 2-(methylthio)benzaldehyde oxime was added under nitrogen atmosphere. 25.2 g (0.21 mol) Of thionyl chloride was added dropwise thereto while stirring at a temperature of from −10° to −15° C. and allowed to react for 1 hour at the same temperature. After the termination of the reaction, the reaction mixture was heated to room temperature and subjected to distilling off of the solvent and then to distillation under reduced pressure to give 26.2 g of 1,2-benzisothiazole (boiling point: 115° to 116° C./15 mm Hg, melting point: 39° to 40° C.). The yield was 97% to the 2-(methylthio)benzaldehyde oxime.

EXAMPLES 2 TO 6

Synthesis of 1,2-Benzisothiazoles

The same procedures as in Example 1 were followed except that 2-(alkylthio)benzaldehyde oximes were changed to those shown in Table 1 which were used as the starting materials, and the corresponding 1,2-benzisothiazoles were obtained. The yields to the respective starting materials are shown in Table 1.

Depending on the physical properties of respective 1,2-benzisothiazoles obtained, the method for isolation, i.e., direct crystallization or extraction and subsequent recrystallization, was adopted.

TABLE 1

| Examples | 2-(Alkylthio)benzaldehyde oximes | 1,2-Benzisothiazoles | Yields (%)* |
|---|---|---|---|
| 2 | 2-(tert-Butylthio)-benzaldehyde oxime | 1,2-Benzisothiazole | 94 |
| 3 | 5-Methyl-2-(ethylthio)-benzaldehyde oxime | 5-Methyl-1,2-benzisothiazole | 95 |
| 4 | 4-Methoxy-2-(methylthio)-benzaldehyde oxime | 6-Methoxy-1,2-benzisothiazole | 93 |
| 5 | 2-Methylthio-3-nitrobenzaldehyde oxime | 7-Nitro-1,2-benzisothiazole | 91 |
| 6 | 4-Chloro-2-(methylthio)-benzaldehyde oxime | 6-Chloro-1,2-benzisothiazole | 95 |

*Yields of 1,2-benzisothiazoles to the 2-(alkylthio)benzaldehyde oximes.

EXAMPLE 7

The same procedures as in Example 1 were followed except that 32.2 g (0.21 mol) of phosphorus oxychloride was added instead of thionyl chloride to give 20.3 g of 1,2-benzisothiazole. The yield was 75% to the 2-(methylthio)benzaldehyde oxime.

EXAMPLE 8

Synthesis of 3-Chloro-1,2-benzisothiazole

In a 300 ml four-necked flask equipped with a stirrer, a thermometer, and a condenser, 100 g of monochlorobenzene was placed in advance, to which 27.0 g (0.2 mol) of 1,2-benzisothiazole was added under nitrogen atmosphere. 32.4 g (0.22 mol) Of sulfuryl chloride was added dropwise thereto while stirring at a temperature of from 70° to 80° C. and allowed to react for 1 hour at the same temperature. After the termination of the reaction, the reaction mixture was subjected to distilling off of the solvent and then to distillation under reduced pressure to give 32.5 g of 3-chloro-1,2-benzisothiazole (boiling point: 116° to 118° C./5 mm Hg, melting point: 38° to 40° C.). The yield was 96% to the 1,2-benzisothiazole.

EXAMPLES 9 TO 12

Synthesis of 3-Halo-1,2-benzisothiazoles

The same procedures as in Example 8 were followed except that the starting material and halogenating agent were respectively change to those in Table 2, and 3-halo-1,2-benzisothiazoles corresponding to respective starting materials were obtained. The yields to the respective starting materials are shown in Table 2. Depending on the physical properties of the respective 3-halo-1,2-benzisothiazoles obtained, the method for isolation, i.e., direct crystallization or extraction and subsequent recrystallization, was adopted.

TABLE 2

| Examples | 1,2-Benzisothiazoles | Halogenating Agents | 3-Halo-1,2-benzisothiazoles | Yields* (%) |
|---|---|---|---|---|
| 9 | 1,2-Benzisothiazole | Bromine | 3-Bromo-1,2-benzisothiazole | 95 |
| 10 | 5-Methyl-1,2-benzisothiazole | Chlorine | 3-Chloro-5-methyl-1,2-benzisothiazole | 94 |
| 11 | 6-Methoxy-1,2-bebzisothiazole | Sulfuryl chloride | 3-Chloro-6-methoxy-1,2-benzisothiazole | 96 |
| 12 | 7-Nitro-1,2-benzisothiazole | Chlorine | 3-Chloro-7-nitro-1,2-benzisothiazole | 93 |

* Yields of 3-halo-1,2-benzisothiazoles to the 1,2-benzisothiazoles.

EXAMPLE 13

Synthesis of 3-Chloro-1,2-benzisothiazole (One-pot Process)

In a 300 ml four-necked flask equipped with a stirrer, a thermometer, and a condenser, 100 g of monochlorobenzene was placed in advance, to which 33.4 g (0.2 mol) of 2-(methylthio)benzaldehyde oxime was added under nitrogen atmosphere. 25.2 g (0.21 mol) Of thionyl chloride was added dropwise thereto while stirring at a temperature of from −10° to −15° C. and allowed to react for 1 hour at the same temperature. After the termination of the reaction, 15.6 g (0.22 mol) of chlorine was continuously blown into the reaction mixture containing 1,2-benzisothiazole while stirring at a temperature of from 70° to 80° C. and allowed to react for 1 hour at the same temperature. After the termination of the reaction, the reaction mixture was subjected to distilling off of the solvent and then to distillation under reduced pressure to give 32.6 g of 3-chloro-1,2-benzisothiazole. The yield was 96% to the 2-(methylthio) benzaldehyde oxime.

EXAMPLE 14

Synthesis of 1-(1,2-Benzisothiazole-3-yl)piperazine (One-pot Process)

In a 300 ml four-necked flask equipped with a stirrer, a thermometer, and a condenser, 100 g of monochlorobenzene was placed in advance, to which 33.4 g (0.2 mol) of 2-(methylthio)benzaldehyde oxime was added under nitrogen atmosphere. 25.2 g (0.21 mol) Of thionyl chloride was added dropwise thereto while stirring at a temperature of from −10° to −15° C. and allowed to react for 1 hour at the same temperature. After the termination of the reaction, 15.6 g (0.22 mol) of chlorine was continuously blown into the reaction mixture while stirring at a temperature of from 70° to 80° C. and allowed to react for 1 hour at the same temperature. After the termination of the reaction, the solvent was distilled off to give 33.1 g of 3-chloro-1,2-benzisothiazole.

Subsequently, 49.0 g (0.57 mol) of piperazine was added under nitrogen atmosphere. The reaction mixture was heated to 100° C. and allowed to react for 2 hours at the same temperature. After the reaction mixture was added to 100 g of water, the precipitate was filtered and dried to give 32.3 g of crude crystals of 1-(1,2-benzisothiazol-3-yl)piperazine. The crude crystals were recrystallized from toluene to give 26.3 g of pure crystals of 1-(1,2-benzisothiazol-3-yl) piperazine. The yield was 60% to the 2-(methylthio) benzaldehyde oxime.

INDUSTRIAL APPLICABILITY

By the production methods of the present invention, 1,2-benzisothiazoles and 3-halo-1,2-benzisothiazoles, useful intermediates for pharmaceutical compositions, such as psychotropic agents, and 1-(1,2-benzisothiazole-3-yl) piperazines synthesized therefrom can be obtained in a high yield without using expensive starting materials by shorter and simpler processes than conventional methods.

We claim:

1. A method for producing a 1,2-benzisothiazole represented by the general formula (II), characterized by treating a 2-(alkylthio)benzaldehyde oxime represented by the general formula (I):

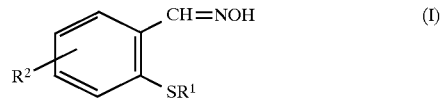

wherein $R^1$ represents an alkyl group having 1 to 4 carbon atoms; and $R^2$ represents a hydrogen atom, an alkyl group having 1 to 4 carbon atoms, an alkoxy group having 1 to 4 carbon atoms, a nitro group, a carboxyl group or an ester thereof, or a halogen atom,
with a halogen compound to give a 1,2-benzisothiazole represented by the general formula (II):

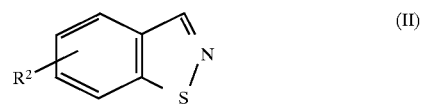

wherein $R^2$ has the same definition as $R^2$ in the general formula (I).

2. The method according to claim 1, wherein the halogen compound is thionyl chloride.

3. The method according to claim 1, wherein the halogen compound is phosphorus oxychloride.

4. The method according to any one of claims 1 to 3, wherein the compound represented by the general formula (I) is 2-(methylthio)benzaldehyde oxime.

5. A method for producing a 3-halo-1,2-benzisothiazole represented by the general formula (III), characterized by reacting a 1,2-benzisothiazole represented by the general formula (II):

wherein $R^2$ represents a hydrogen atom, an alkyl group having 1 to 4 carbon atoms, an alkoxy group having 1 to 4 carbon atoms, a nitro group, or a carboxyl group or an ester thereof, with a halogenating agent to give a 3-halo-1,2-benzisothiazole represented by the general formula (III):

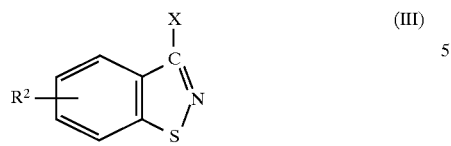

wherein X represents a chlorine atom or a bromine atom; and $R^2$ has the same definition as $R^2$ in the general formula (II).

6. The method according to claim 5, wherein the halogenating agent is chlorine or bromine.

7. The method according to claim 5, wherein the halogenating agent is sulfuryl chloride.

8. The method according to claim 5, 6, or 7, wherein the compound represented by the general formula (II) is 1,2-benzisothiazole.

9. A method for producing a 3-halo-1,2-benzisothiazole represented by the general formula (III), characterized by
treating a 2-(alkylthio)benzaldehyde oxime represented by the general formula (I):

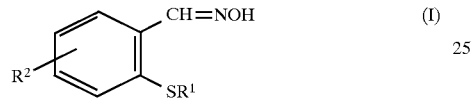

wherein $R^1$ represents an alkyl group having 1 to 4 carbon atoms; and $R^2$ represents a hydrogen atom, an alkyl group having 1 to 4 carbon atoms, an alkoxy group having 1 to 4 carbon atoms, a nitro group, a carboxyl group or an ester thereof, or a halogen atom, with a halogen compound to give a 1,2-benzisothiazole represented by the general formula (II):

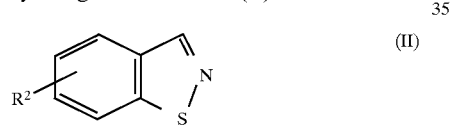

wherein $R^2$ has the same definition as $R^2$ in the general formula (I); and reacting the obtained 1,2-benzisothiazoles with a halogenating agent to give a 3-halo-1,2-benzisothiazole represented by the general formula (III):

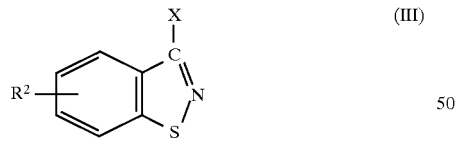

wherein X represents a chlorine atom or a bromine atom;

and $R^2$ has the same definition as $R^2$ in the general formula (II).

10. The method according to claim 9, wherein the halogen compound is thionyl chloride.

11. The method according to claim 9, wherein the halogen compound is phosphorus oxychloride.

12. The method according to claim 9, wherein the halogenating agent is chlorine or bromine.

13. The method according to claim 9, wherein the halogenating agent is sulfuryl chloride.

14. The method according to claim 9, 10, 11, 12 or 13, wherein the compound represented by the general formula (I) is 2-(methylthio)benzaldehyde oxime.

15. A method for producing a 1-(1,2-benzisothiazol-3-yl)piperazine represented by the general formula (V), characterized by treating a 2-(alkylthio)benzaldehyde oxime represented by the general formula (I):

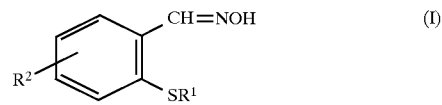

wherein $R^1$ represents an alkyl group having 1 to 4 carbon atoms; and $R^2$ represents a hydrogen atom, an alkyl group having 1 to 4 carbon atoms, an alkoxy group having 1 to 4 carbon atoms, a nitro group, a carboxyl group or an ester thereof, or a halogen atom, with a halogen compound to give a 1,2-benzisothiazole represented by the general formula (II):

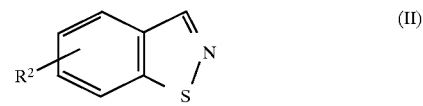

wherein $R^2$ has the same definition as $R^2$ in the general formula (I);

reacting the obtained 1,2-benzisothiazoles with a halogenating agent to give a 3-halo-1,2-benzisothiazole represented by the general formula (III):

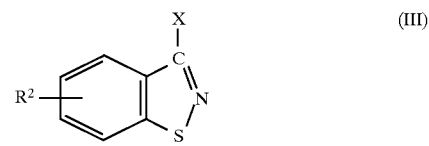

wherein X represents a chlorine atom or a bromine atom;

and $R^2$ has the same definition as $R^2$ in the general formula (I); and reacting the 3-halo-1,2-benzisothiazoles with a piperazine represented by the general formula (IV):

wherein $R^3$ represents a hydrogen atom, an alkyl group having 1 to 6 carbon atoms, or a substituted alkylene group having 1 to 6 carbon atoms, to give a 1-(1,2-benzisothiazol-3-yl)piperazine represented by the general formula (V):

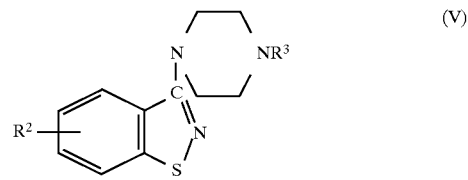

wherein $R^2$ has the same definition as $R^2$ in the general formula (I); and $R^3$ has the same definition as $R^3$ in the general formula (IV).

* * * * *